United States Patent
Fox et al.

(10) Patent No.: US 6,418,183 B1
(45) Date of Patent: Jul. 9, 2002

(54) METHODS AND APPARATUS FOR TWO-PASS CT IMAGING

(75) Inventors: Stanley H. Fox; Jiang Hsieh, both of Brookfield, WI (US)

(73) Assignee: GE Medical Systems Global Technology Company, LLP, Waukesha, WI (US)

( * ) Notice: Subject to any disclaimer, the term of this patent is extended or adjusted under 35 U.S.C. 154(b) by 0 days.

(21) Appl. No.: 09/749,821

(22) Filed: Dec. 28, 2000

(51) Int. Cl.[7] .................................................. A61B 6/03
(52) U.S. Cl. ............................. 378/15; 378/19; 378/901
(58) Field of Search ........................ 378/4, 8, 15, 901, 378/19

(56) References Cited

U.S. PATENT DOCUMENTS

| | | | |
|---|---|---|---|
| 4,712,178 A | 12/1987 | Tuy et al. | |
| 5,598,453 A | 1/1997 | Baba et al. | |
| 6,023,494 A | * 2/2000 | Senzig et al. | 378/4 |
| 6,084,227 A | 7/2000 | Rhoads | |
| 6,215,841 B1 | 4/2001 | Hsieh | |
| 6,217,214 B1 | * 4/2001 | Cabral et al. | 378/196 |
| 6,256,368 B1 | * 7/2001 | Hsieh et al. | 378/8 |
| 6,272,200 B1 | 8/2001 | Pan et al. | |

* cited by examiner

Primary Examiner—Drew A. Dunn
(74) Attorney, Agent, or Firm—Carl B. Horton, Esq.; Armstrong Teasdale LLP

(57) ABSTRACT

One aspect of the present invention is a method for imaging a volume of a patient with a computed tomographic (CT) imaging system. The method includes steps of: scanning a volume of a patient with a first, full field of view (FOV) scan to acquire first projection data; scanning a smaller volume of the patient with a second, restricted FOV scan to acquire second projection data; estimating an amount of shift between the first projection data and the second projection data resulting from patient movement; and blending first projection data with second projection data in accordance with the estimated amount of shift to estimate projections of the second scan.

18 Claims, 2 Drawing Sheets

METHODS AND APPARATUS FOR TWO-PASS CT IMAGING

BACKGROUND OF THE INVENTION

This invention relates generally to methods and apparatus for CT image reconstruction, and more particularly to methods and apparatus for utilizing more than one scan for reconstruction of CT images that are particularly advantageous for cardiac CT imaging.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". Each discrete attenuation measurement in a view corresponding to a given detector angle $\gamma$ is referred to as being obtained from a detector "channel." A "scan" of the object comprises a set of views made at different gantry angles, or view angles, during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

In known cardiac CT studies, two scans are performed, one with and one without contrast injection. In these studies, a full field of view (FOV) scan is performed both times, because a significant amount of time elapses between the two scans, and patient motion can occur. In addition, breath-hold levels of the two scans may be different. It would be desirable to minimize the radiation dose to a patient when performing such a study.

BRIEF SUMMARY OF THE INVENTION

There is therefore provided, in one embodiment of the present invention, a method for imaging a volume of a patient with a computed tomographic (CT) imaging system having a radiation source and a detector array opposing one another on a rotating gantry and configured so that radiation from the radiation source passing through a patient impinges on the detector array. The method includes steps of: scanning a volume of a patient with a first, full field of view (FOV) scan to acquire first projection data; scanning a smaller volume of the patient with a second, restricted FOV scan to acquire second projection data; estimating an amount of shift between the first projection data and the second projection data resulting from patient movement; and blending first projection data with second projection data in accordance with the estimated amount of shift to estimate projections of the second scan.

Embodiments of the present invention minimize the radiation dose to a patient when performing cardiac studies in that the second scan can be performed using a radiation beam collimated to restrict its coverage to a lesser portion of the patient.

DETAILED DESCRIPTION OF THE INVENTION

Figure 1:
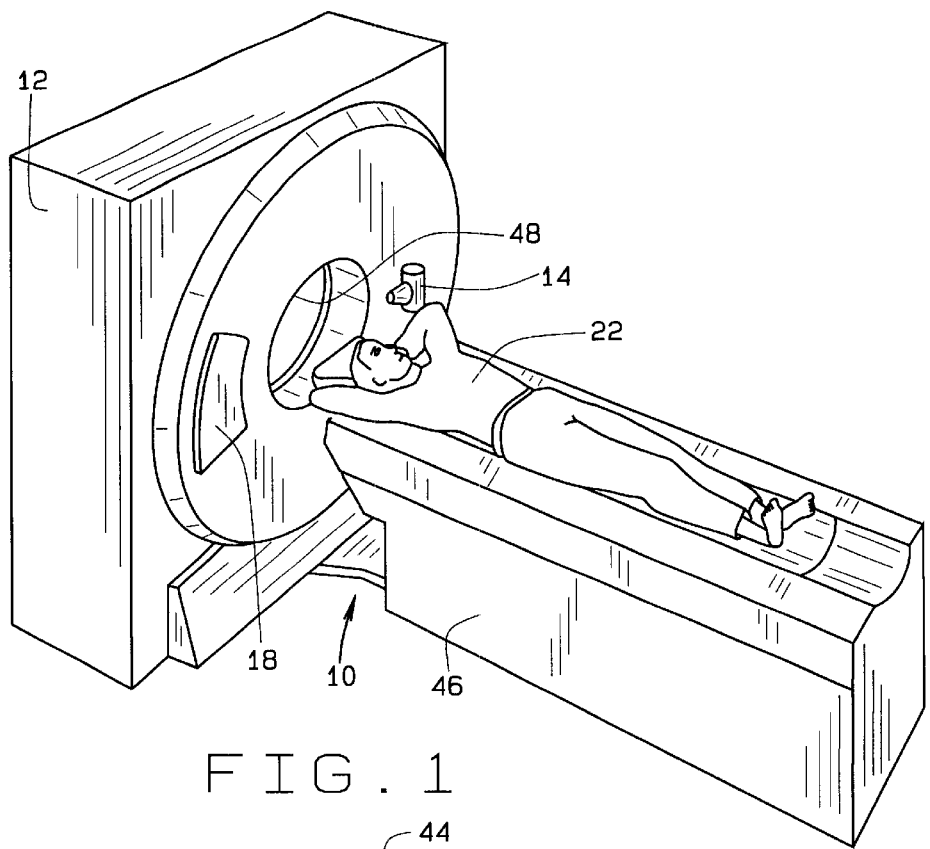
FIG. 1 is a pictorial view of a CT imaging system.
Figure 2:
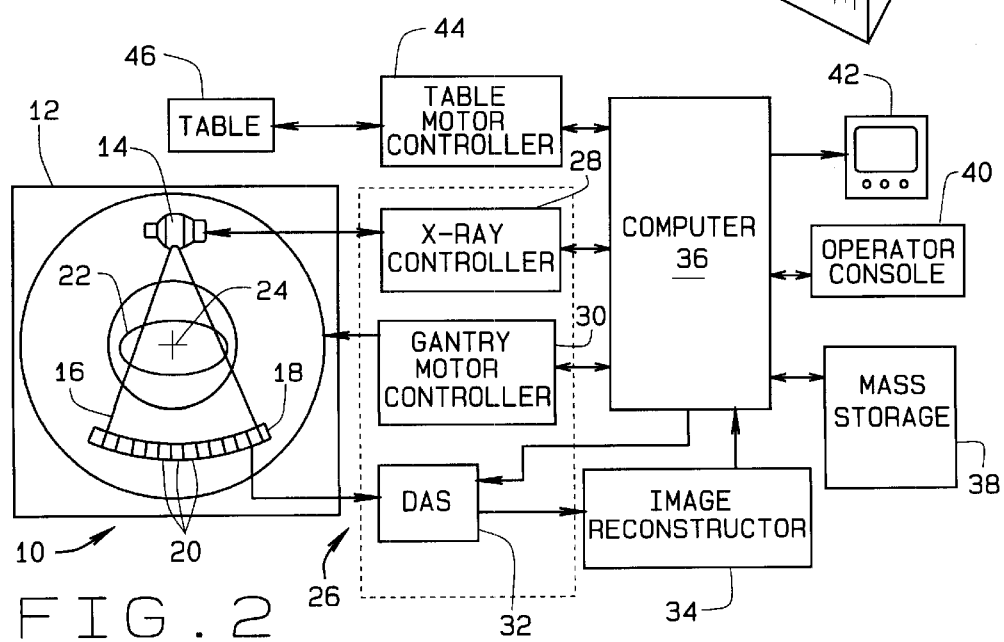
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object 22, for example a medical patient. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24. Detector array 18 may be fabricated in a single slice or multi-slice configuration. In a multi-slice configuration, detector array 18 has a plurality of rows of detector elements 20, only one of which is shown in FIG. 2.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

Figure 3:
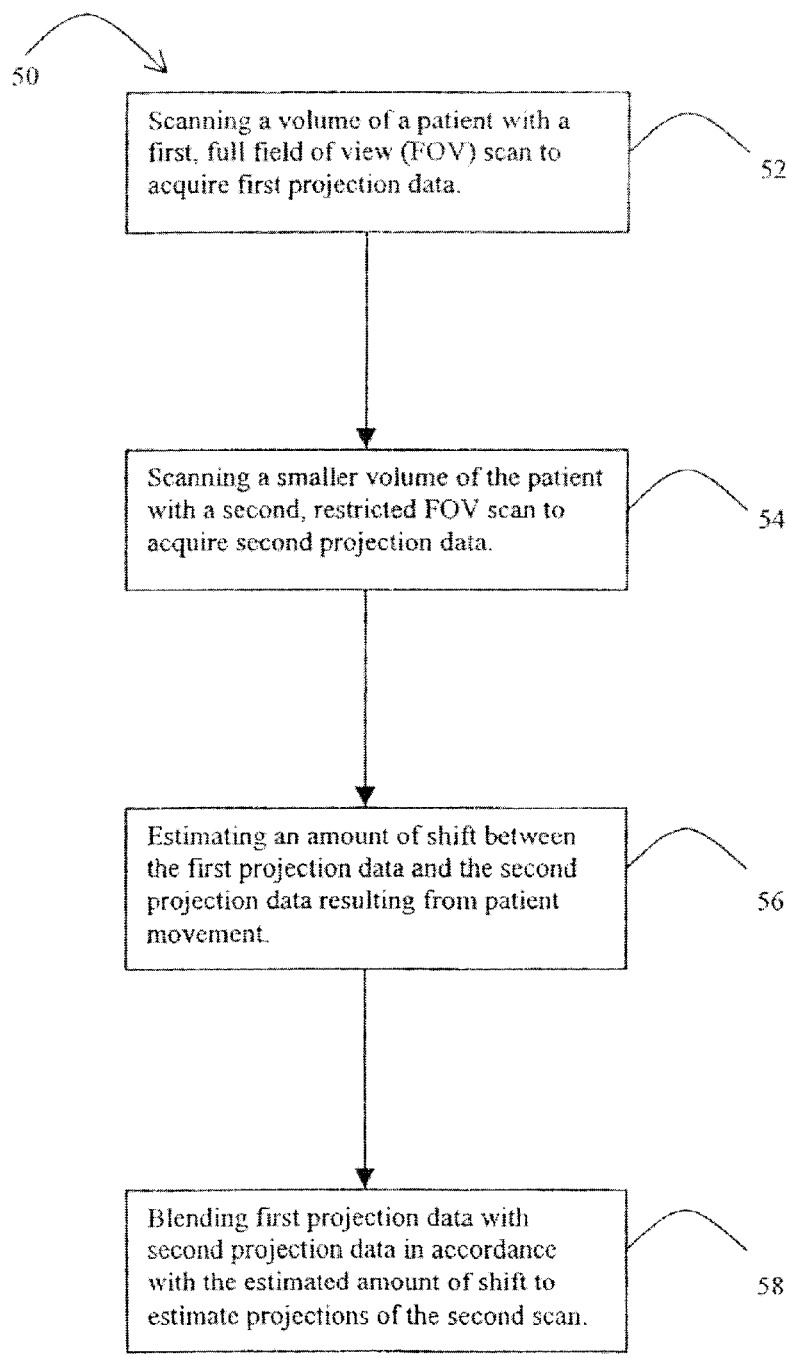
FIG. 3 is a flow chart diagram illustrating a method for scanning a volume of a patient.

FIG. 3 is a flow chart diagram illustrating a method 50 for scanning 52 a volume of a patient with a first, full field of view (FOV) scan to acquire first projection data, scanning 54 a smaller volume of the patient with a second, restricted FOV scan to acquire second projection data, estimating 56 an amount of shift between the first projection data and the second projection data resulting from patient movement, and blending 58 first projection data with second projection data in accordance with the estimated amount of shift to estimate projections of the second scan.

In one embodiment of the present invention, two scans are performed with and without contrast injection. A first scan 52 is acquired with normal full field of view (FOV) exposure. Images acquired during this scan 52 are reconstructed using known standard reconstruction algorithms. After contrast injection, a second scan 54 is performed. For this scan 54, the radiation beam is pre-collimated so that only a region $R_c$ of the patient is exposed. For example, for cardiac CT imaging, this region includes the heart plus a small margin. In another embodiment, exposure is limited to a pre-defined region of interest (e.g., a center 25 cm region) to simplify collimator design.

The projection information outside of $R_c$ of the first scan 52, $P_1(\gamma)$, is used to estimate the projections of the second scan 54, $P_2(\gamma)$. Because significant time elapses between the first scan 52 and the second scan 54, patient motion can occur between the two scans. For example, the breath-hold levels for the two scans are likely to be different. In addition, the patient might shift or move. Therefore, two projections at the same angle cannot simply be patched together to obtain an artifact-free reconstruction. To overcome this difficult, method 50 is used in one embodiment of the present invention.

First, the amount of shift in the projection due to patient movement 56 is estimated by calculating the first and second moments of $P_2(\gamma)$ within $R_c$. In addition, the first and second moments of $P_1(\gamma)$ are determined for the same projection angle, for the same number of channels. However, the calculation is performed for the neighboring n-channel shift regions. For example, assume that $R_c$ is defined by detector channels $\gamma_L \leq \gamma < \gamma_H$. For the second scan 54, a series of first and second moments are determined for a region $\gamma_L + \eta \leq \gamma < \gamma_H + \eta$, where $-\eta_s \leq \eta \leq \eta_s$ and $\eta_s$ is a parameter that defines the search region. A value of $\eta$ is selected that has the best match to the second scan. In one embodiment, additional constraints are placed on $\eta$. For example, $\eta$ is constrained so as not to change by more than a predetermined amount from view to view. The value of $\eta$ determines the projection data of the first set from which an estimate of the projection of the second scan outside $R_c$ is made. In general, $\eta$ varies with projection angle.

Next, projection blending 58 is performed between the two projections. In one embodiment, blending 58 is performed to produce a projection $P(\gamma)$ written:

$$P(\gamma)=[1-\theta(\gamma)]P_1(\gamma+\eta)+\theta(\gamma)P_2(\gamma)$$

where $$\theta(\gamma)=3w^2(\gamma)+2w^3(\gamma)$$

and $w(\gamma) = \begin{cases} \frac{\gamma+\gamma_L}{\delta}, & -\gamma_L \leq \gamma < -\gamma_L+\delta \\ 1, & -\gamma_L+\delta \leq \gamma < \gamma_H-\delta \\ \frac{\gamma_H-\gamma}{\delta}, & \gamma_H-\delta \leq \gamma < \gamma_H \\ 0, & \text{otherwise.} \end{cases}$ In these equations, $\delta$ is a parameter that defines the width of the blending region. It is a parameter that depends upon, and is determined by, the value of $\eta$. In general, the larger the magnitude of $\eta$, the larger the value of $\delta$.

In one embodiment of the present invention, the steps required to estimate shift due to patient movement, the calculation of the moments and the blending 58 of the projection data are performed by image reconstructor 34 of computed tomographic imaging system 10. For example, image reconstructor 34 includes a software or firmware program providing the instructions to perform these steps. In another embodiment of the present invention, some or all of these steps are performed in a separate device, such as a computer or imaging workstation.

While the invention has been described in terms of various specific embodiments, those skilled in the art will recognize that the invention can be practiced with modification within the spirit and scope of the claims.

What is claimed is:

1. A method for imaging a volume of a patient with a computed tomographic (CT) imaging system having a radiation source and a detector array opposing one another on a rotating gantry and configured so that radiation from the radiation source passing through a patient impinges on the detector array; said method comprising the steps of:

scanning a volume of a patient with a first, full field of view (FOV) scan to acquire first projection data;

scanning a smaller volume of the patient with a second, restricted FOV scan to acquire second projection data;

estimating an amount of shift between the first projection data and the second projection data resulting from patient movement; and blending first projection data with second projection data in accordance with the estimated amount of shift to estimate projections of the second scan.

2. A method in accordance with claim 1 further comprising the step of contrast injecting the patient between the first scan and the second scan.

3. A method in accordance with claim 1 wherein the CT imaging system further comprises a pre-patient collimator and said step of scanning a smaller volume of the patient comprises the step of collimating the radiation from the radiation source so that only a region $R_c$ of the patient is exposed to radiation, and region $R_c$ is smaller than a region of the patient exposed during the first, full FOV scan.

4. A method in accordance with claim 3 wherein estimating an amount of shift between the first projection data and the second projection data comprises determining moments of the first projection data and of the second projection data.

5. A method in accordance with claim 4 wherein said step of determining moments comprises the steps of determining a first moment and a second moment of the first projection data inside the restricted FOV and determining a first moment and a second moment of the second projection data.

6. A method in accordance with claim 5 wherein the first projection data comprises data corresponding to a first number of detector channels, the second projection data comprises data corresponding to a second number of detector channels, and further wherein said step of determining moments is performed for the same number of channels for the second projection data and for the first projection data.

7. A method in accordance with claim 5 wherein the region $R_c$ is defined by detector channels $\gamma_L \leq \gamma < \gamma_H$, and said step of determining moments for the second scan comprises calculating a series of first moments and second moments for a region $\gamma_L+\eta \leq \gamma < \gamma_H+\eta$, where $-\eta_S \leq \eta \leq \eta_S$ and $\eta_S$ is a parameter defining a search region.

8. A method in accordance with claim 7 further comprising the step of placing a predetermined limit on changes in $\eta$ from view to view.

9. A method in accordance with claim 7 wherein said step of blending first projection data with second projection data comprises the step of blending to produce a projection P(γ) written:

$$P(\gamma)=[1-\theta(\gamma)]P_1(\gamma+\eta)+\theta(\gamma)P_2(\gamma),$$

where $$\theta(\gamma)=3w^2(\gamma)+2w^3(\gamma),$$

$$w(\gamma) = \begin{cases} \dfrac{\gamma+\gamma_L}{\delta}, & -\gamma_L \leq \gamma < -\gamma_L + \delta \\ 1, & -\gamma_L + \delta \leq \gamma < \gamma_H - \delta \\ \dfrac{\gamma_H - \gamma}{\delta}, & \gamma_H - \delta \leq \gamma < \gamma_H \\ 0, & \text{otherwise,} \end{cases}$$

and δ is a parameter that defines a width of a blending region.

10. A method in accordance with claim 9 further comprising the step of contrast injecting the patient between the first scan and the second scan.

11. A method in accordance with claim 10 wherein the region $R_c$ includes the heart of the patient.

12. A computed tomographic (CT) imaging system having a radiation source and a detector array opposing one another on a rotating gantry and configured so that radiation from the radiation source passing through a patient impinges on the detector array; said imaging system further configured to:
scan a volume of a patient with a first, full field of view (FOV) scan to acquire first projection data;
scan a smaller volume of the patient with a second, restricted FOV scan to acquire second projection data;
estimate an amount of shift between the first projection data and the second projection data resulting from patient movement; and
blend first projection data with second projection data in accordance with the estimated amount of shift to estimate projections of the second scan.

13. An imaging system in accordance with claim 12 wherein the CT imaging system further comprises a pre-patient collimator, and to scan a smaller volume of the patient, said CT imaging system is configured to collimate the radiation from the radiation source so that a region $R_c$ of the patient is exposed, and region $R_c$ is smaller than a region of the patient exposed during the first, full FOV scan.

14. An imaging system in accordance with claim 13 wherein to estimate an amount of shift between the first projection data and the second projection data, said imaging system is configured to determine moments of the first projection data and of the second projection data.

15. An imaging system in accordance with claim 14 wherein to determine moments of the first projection data and of the second projection data, said imaging system is configured to determine a first moment and a second moment of the first projection data inside the restricted FOV and to determine a first moment and a second moment of the second projection data.

16. An imaging system in accordance with claim 15 wherein the first projection data comprises data corresponding to a first number of detector channels, the second projection data comprises data corresponding to a second number of detector channels,
and said imaging system is configured to utilize the same number of channels for the second projection data and for the first projection data in determining moments of the first projection data and of the second projection.

17. An imaging system in accordance with claim 15 wherein the region $R_c$ is defined by detector channels $\gamma_L \leq \gamma < \gamma_H$, and wherein to determine moments for the second scan, said imaging system is configured to calculate a series of first moments and second moments for a region $\gamma_L + \eta \leq \gamma < \gamma_H + \eta$, where $-\eta_S \leq \eta \leq \eta_S$ and $\eta_S$ is a parameter defining a search region.

18. An imaging system in accordance with claim 17 wherein to blend first projection data with second projection data, said imaging system is configured to produce a projection P(γ) written:

$$P(\gamma)=[1-\theta(\gamma)]P_1(\gamma+\eta)+\theta(\gamma)P_2(\gamma),$$

where $$\theta(\gamma)=3w^2(\gamma)+2w^3(\gamma),$$

$$w(\gamma) = \begin{cases} \dfrac{\gamma+\gamma_L}{\delta}, & -\gamma_L \leq \gamma < -\gamma_L + \delta \\ 1, & -\gamma_L + \delta \leq \gamma < \gamma_H - \delta \\ \dfrac{\gamma_H - \gamma}{\delta}, & \gamma_H - \delta \leq \gamma < \gamma_H \\ 0, & \text{otherwise,} \end{cases}$$

and δ is a parameter that defines a width of a blending region.

* * * * *